United States Patent [19]

Buchner et al.

[11] 4,443,862
[45] Apr. 17, 1984

[54] ULTRASONIC SIGNAL APPARATUS WITH MULTIPLEXER FOR SELECTIVELY LOADING VIDEO LINE SEGMENTS INTO A PARALLEL-PARTITIONED IMAGE STORE

[75] Inventors: Klaus Buchner, Kleinsendelbach; Ulrich Saugeon, Erlangen, both of Fed. Rep. of Germany

[73] Assignee: Siemens Aktiengesellschaft, Berlin & Munich, Fed. Rep. of Germany

[21] Appl. No.: 256,723

[22] Filed: Apr. 23, 1981

[30] Foreign Application Priority Data

May 2, 1980 [DE] Fed. Rep. of Germany ....... 3017027

[51] Int. Cl.³ ............................................. G06F 15/42
[52] U.S. Cl. .................................. 364/900; 364/415; 73/626; 128/660
[58] Field of Search ... 364/200 MS File, 900 MS File, 364/521, 413–415; 340/750, 799, 802; 73/620, 626, 606, 607; 128/660

[56] References Cited

U.S. PATENT DOCUMENTS

| | | | |
|---|---|---|---|
| 4,111,055 | 9/1978 | Skidmore | 73/620 |
| 4,121,250 | 10/1978 | Huelsman . | |
| 4,206,654 | 6/1980 | Keller et al. | 73/620 |
| 4,257,256 | 3/1981 | Yoshikawa | 73/626 |
| 4,258,575 | 3/1981 | Buchner | 73/626 |
| 4,271,842 | 6/1981 | Specht et al. | 128/661 |
| 4,373,395 | 2/1983 | Borburgh et al. | 73/607 |
| 4,381,675 | 5/1983 | Roberts et al. | 73/620 |

OTHER PUBLICATIONS

Ken-Ichi Ito et al., "A Real-Time Ultrasonic Diagnostic System for Dynamic and Still Images: Wireless Echovision", New Technology, JEE, Dec. 1977, pp. 20–26 and Contents.

Primary Examiner—James D. Thomas
Assistant Examiner—Archie E. Williams, Jr.
Attorney, Agent, or Firm—Hill, Van Santen, Steadman & Simpson

[57] ABSTRACT

Ultrasonic signals, for example, are provided with a fast-acting store which, at the same time, allows maximum flexibility in addressing. The signals arriving at the signal inputs of the signal store are apportioned into channel sections, and the channel sections occurring after each other in time may each be read in parallel formation into section addresses of the signal store. The section addresses may be read out again orthogonally following each other in time in such a sequence that, in combination, the original signals are again obtained.

21 Claims, 2 Drawing Figures

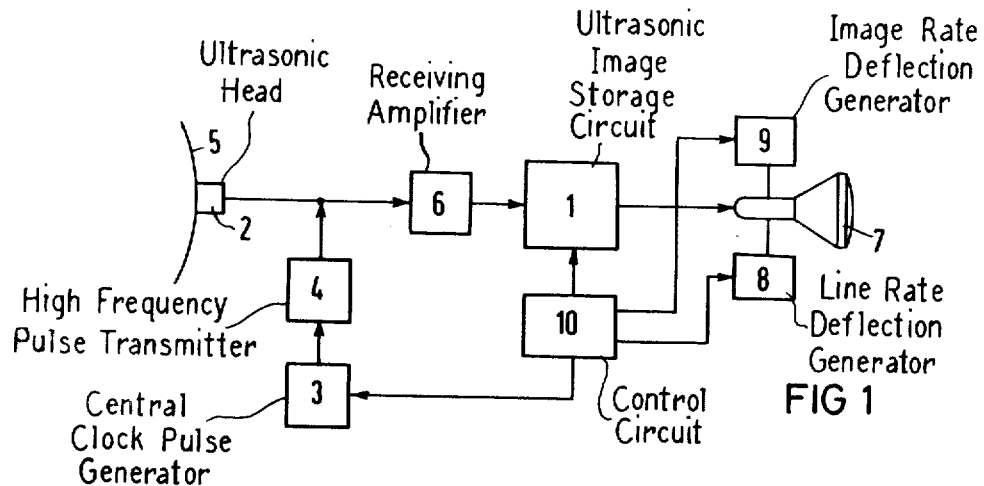
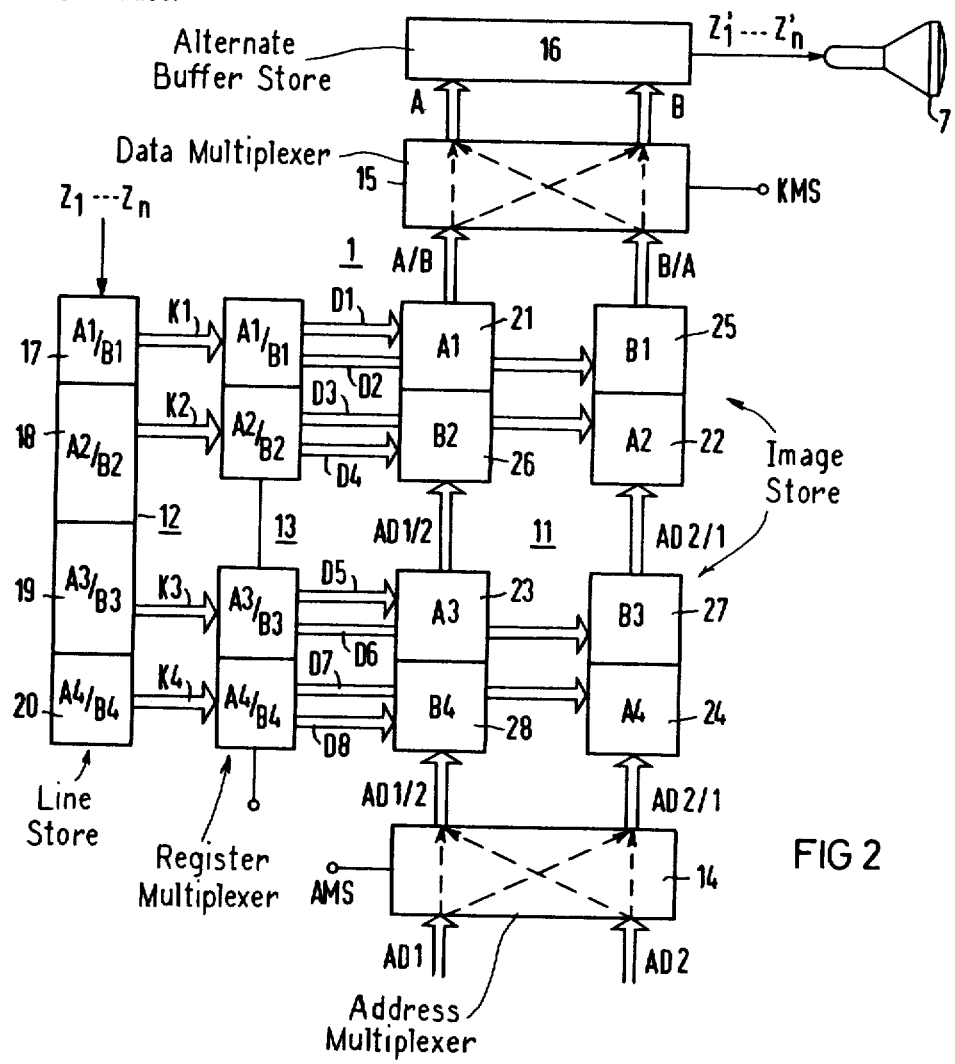

ULTRASONIC SIGNAL APPARATUS WITH MULTIPLEXER FOR SELECTIVELY LOADING VIDEO LINE SEGMENTS INTO A PARALLEL-PARTITIONED IMAGE STORE

BACKGROUND OF THE INVENTION

The invention relates to an apparatus for the storing of signals, more particularly ultrasonic signals, having a signal store with signal inputs for the read in of the signals and signal outputs for the read out of the stored signals, preferably to a recording device. The term signals includes in the broadest sense any signals, such as physiological signals (ECG, etc.), x-ray signals and more particularly ultrasonic signals in the medical field or any similar signals in the general technical field.

A great many arrangements of this type are already known specifically from ultrasonic image technique, for example German Offenlegungsschrift No. 26 19 684, German Auslegeschrift No. 24 17 946, U.S. Pat. No. 4,121,250, and the paper entitled: "A real-time Ultrasonic Diagnostic System for Dynamic and Still Images: Wireless Echovision" by K. I. Ito et al from the JEE Journal, December 1977, pages 20 to 26, which arrangements operate with a signal store which is designed in the conventional manner as an orthogonal frame store. The significant characteristic of this orthogonal store is that the signals arriving are read into the store in series and then read out again orthogonally to the read-in direction. However, experience has shown that the serial read-in results in relatively long image forming times so that a conversion mode from the slow ultrasonic image to the more rapid video image is produced, but this is still not always fast enough and thus leads to image flicker. Moreover, the conventional type of orthogonal store also requires a relatively rigid addressing scheme during the relatively slow read-in. This type of store is thus insufficiently flexible with regard to the great variety of application required.

SUMMARY OF THE INVENTION

The object of the present invention is to design an apparatus of the initially named type which is provided with a faster acting store which at the same time allows maximum flexibility in the addressing.

This object is achieved according to the invention in that signals arriving at the signal inputs of the signal store are apportioned into channel sections, and in that channel sections arriving after one another in time may each be read in parallel formation into section addresses of the signal store, and in that the section addresses may be read out again orthogonally following one another in time in such a sequence that, in combination, the original signals are reproduced.

According to the invention the signals arriving are now apportioned in channel sections which are in turn read into the actual signal store in parallel formation. This parallel transfer shortens the write-in time, which in turn also shortens the image formation time. Image flicker is thus largely avoided. The signal store used may be organized for any type of addressing. A rigid addressing scheme such as that needed with conventional orthogonal stores is therefore avoided so that the signal store as a whole may be put to more varied use.

In an advantageous development of the invention the section addresses of signals following each other in time are nested in cross-wise parallel fashion in the signal store so that when the signal sections are read out orthogonally according to the sequence of arrival they are automatically combined in correct time sequence to the forms of the original signals. The special type of transverse nesting of signal sections in the signal store allows signal data to be written into the store approximately four times more quickly. This gain by the time factor four thus makes possible a particularly fast real-time conversion.

In a further advantageous development of the invention, the signal sections should be written in and read out in programmable formation. In this connection the read-out process in particular should be programmable so that specific signal sections can be read out to different representation modes. More particularly, the signal store in this connection may be an ultrasonic image store which can be programmed so that a single ultrasonic image or several ultrasonic images can be read in. When there are several ultrasonic images the read-out should take place according to program so that the images can be represented simultaneously in any configuration on an image display device, more particularly a cathode ray tube. This form of representation is not possible with conventional orthogonal stores at the high image frequency desired.

Further advantages and details of the invention will be seen in the following description of an exemplary embodiment with reference to the accompanying drawing sheet in connection with the remaining subclaims; and other objects, features and advantages will be apparent from this detailed disclosure and from the appended claims.

BRIEF DESCRIPTION OF THE DRAWINGS

FIG. 1 shows the application of the invention with ultrasonic image devices, in the form of the basic circuit diagram; and FIG. 2 shows the invention in the form of the basic circuit diagram.

DETAILED DESCRIPTION

In FIG. 1 the apparatus for the storing of the ultrasonic signals is represented as a block 1. This block 1 is specifically a component of an ultrasonic image display device. This image display device therefore comprises in the usual way an ultrasonic head 2 (for example a mechanically displaceable or pivotable transducer or ultrasonic array) to which high frequency pulses of an HF-pulse transmitter 4 are delivered in synchronism with a central clock pulse generator 3. The sonic head then radiates ultrasonic transmission pulses into an examination subject 5. When the examination subject 5 is scanned line-by-line (for example as a result of mechanical displacement or pivoting of the sonic head 2 or as a result of the electronic stepping of the beam along the individual elements of a transducer element arrangement as in the case of an ultrasonic array) the ultrasonic signals reflected therein at different internal points are received again by the ultrasonic head 2 and converted back into electrical echo signals. The echo signals are amplified in a receiving amplifier 6 and are then read into the store arrangement 1 and out again in the manner according to the invention. The read-out is to a cathode ray tube 7 with a line rate deflection generator 8 and an image rate deflection generator 9 for the formation of an echo visual image. The overall control is provided by a control circuit 10.

The construction and mode of operation of the store arrangement 1 are now described in more detail in the following with reference to the basic circuit diagram of FIG. 2.

In FIG. 2 the store arrangement 1 comprises an image store 11 to which is connected on the input side a line store 12 with a register multiplexer 13. An address multiplexer 14 and also, at the output side, a data multiplexer 15 with alternate buffer store 16 are also associated with the image store 11.

According to FIG. 2 the line store 12 is divided into four sections 17 to 20. During the serial read-in of each ultrasonic line Z1 to Zn, a total of four line sections A1 to A4 and B1 to B4 respectively is therefore available, which sections can now be written-in directly as parallel data by means of parallel read-out (channels K1 to K4) of the register multiplexer 13, and via the signal inputs of the store 11 (data channels D1 to D8) into suitable section addresses 21 to 28.

In the exemplary embodiment of FIG. 2 the image store 11 is divided into $2 \times 4 = 8$ section addresses 21 to 28. For example a basic store plan with $256 \times 256 \times 8$ bits may be chosen for the embodiment in this case. The capacity of all the section addresses of one block 21 to 28 would thus be $128 \times 64$ bits.

In the exemplary embodiment of FIG. 2 the read-in and read-out processes in the store 11 are programmed so that signals arriving at the input of the store are taken over by individual section addresses, nested in parallel and cross-ways. These nested addresses are read out so that when sections are read out in time sequence, the original signal, i.e. in the present case the ultrasonic image, is automatically produced.

This method of cross-wise nested read-in, which enables the read-in speeds to be particularly fast (a speed increased by the factor 4 in comparison with series read-in), is to be explained in more detail with reference to an example which is specifically designed for the representation of at least two ultrasonic images, which occur in time one after the other, simultaneously next to each other or over each other on the image screen of an oscilloscope tube. The program flow of the read-in and read-out again at the store 11 is now such that the first ultrasonic image A, divided into sections A1 to A4, is written into the address sections 21 to 24 in parallel and in sections, this being identified more precisely by the addition of the reference numerals A1 to A4. Correspondingly, a second ultrasonic image B, arriving directly after this in sections B1 to B4 is transferred into the section addresses 25 to 28 of the store 11. The corresponding addresses are identified by B1 to B4. This example clearly shows that the individual sections A1 to A4 of the one ultrasonic image A are nested cross-wise in the addresses with the individual sections B1 to B4 of the second ultrasonic image B in the store 11. As already mentioned above, this nesting allows a particularly fast read-in of ultrasonic images into the store. The read-out of the cross-wise nested sections A1 to A4 and B1 to B4, however, is now controlled by the address multiplexer 14 (input addresses AD1, AD2; output addresses AD1/2, AD2/1; address-multiplex-control signal AMS) in such a way that the address sections A1 to A4 are read out first followed by the address sections B1 to B4 in time sequence via a channel multiplexer 15. In the present case, therefore, image A is obtained first followed by image B, as indicated by the two separate arrow outputs A, B of the channel multiplexer 15. The two images A and B are thus separated again; they may be imaged directly next to each other on one and the same oscilloscope tube 7 after serial line-by-line readout via the outputside line buffer 16 (video lines Z1' to Zn').

It is obvious that it is also possible for the two images to be written in each other and over each other by means of suitably different programming of the flow control. Equally, the flow may also be programmed so that more than two images are read in and read out again simultaneously on the oscilloscope. Obviously, it is also possible to change over to a single image. In this respect a single stored image can also be represented, for example, together with a real-time image. However, the read-in process at the store can also be programmed so that, for example, it is also possible to switch temporarily as required from parallel transfer of signal sections into the signal store to serial transfer. In this connection, the read-in process is of course delayed. However, there is the possibility of representing ultrasonic images of a different type. For example, a B-image may be represented with a TM image.

The exemplary embodiment described is particularly suitable for use during the parallel scanning of subjects. For nonparallel scanning, for example sector scanning, trapezoidal scanning, compound scanning or the like, the invention may also be put to optimum use if the store is reorganized in a simple way with regard to the addressing so that it is adapted to the particular type of application (variable channel sections programmable according to prescribable trigonometric functions and correspondingly adapted addressing in the signal store).

It will be apparent that many modifications and variations may be effected without departing from the scope of the novel concepts and teachings of the present invention.

Supplementary Discussion

To summarize an example pursuant to the embodiment of FIG. 2, for the case of two image series A and B, it may be assumed that each image comprises of the order of 128 lines, and that each line is sampled at 256 points thereof to provide a series of 256 coded numbers (representing 256 picture elements or pixels) per line.

The lines of image A may be designated ZA1 through ZA 128 and the lines of image B may be designated ZB1 through ZB 128. Each picture element may have its echo amplitude represented by an eight-bit coded word, for example, where the blocks 21-28 of image memory 11 are each to have 64 output addresses for the stored values of one line segment. The total capacity of image memory 11 may be $256 \times 256$ words, with eight bits per word. The channel A/B would then have a capacity of eight bits in parallel, and channel B/A would have the same capacity.

Data multiplexer 15 would have output channels A and B of the same capacity, i.e. eight bits in parallel for each channel, and each buffer store of component 16 could have a capacity of one complete line. Thus while the buffer line store for image A was being filled with a line ZA2, the first stored line ZB1 could be displayed at display tube 7. Then as line ZB2 was being transferred to the buffer line store for image B, the stored line ZA2 could be displayed. Each given line of images A and B in the image store 11 can be read out at a rate slightly faster than a desired television line rate at which lines are supplied to display 7, so that each image A and B is displayed at a rate of sixty images per second.

Referring to German application No. P 30 18 129.4 filed May 12, 1980, and to the corresponding U.S. case of Hendle, Maas, and Wolf, U.S. Ser. No. 252,299, filed Apr. 9, 1981, now U.S. Pat. No. 4,398,213 issued Aug. 9, 1983 one image A may be an integrated video image of a vascular system prior to filling with a contrast medium, and the second image series B may represent a real-time summation of subtraction images showing the progress of the contrast medium in the vascular system. Thus images A and B may be selectively superimposed directly on the cathode ray tube 7 when desired.

Using the memory chip organization of a frame memory generally as known in the prior art, image data for two successive picture elements (each of four bits) may provide one word (of eight bits) to match the access speed of the chip output. Then the stored data is read from the memory chips line by line as many times as the number of lines of the TV monitor. The memory chips are such that the data can be written into the memory and read out (at higher speed) independently. FIG. 2 can operate similarly to the known prior art frame memory, except that the addressing is supervised by component 13, FIG. 2, so that pixels No. 1 through 64 of a line segment (e.g. ZA1) are supplied to block A1, (designated by ref. No. 21), pixels No. 65 through 128 are supplied to block A2, pixels No. 129 through 192 are supplied to block A3, and pixels No. 193 through 256 are supplied to block A4. Similarly for each line of image B, the respective line segments of each line are supplied to the respective blocks 25–28.

Read out may be supervised by components 14 and 15, so that the line segments of a line of image A are read out and then the line segments of an image B, and so on as previously described.

We claim as our invention:

1. Apparatus for the storage of successive digital electric signals representing successive video lines, in particular corresponding to ultrasonic images, said apparatus comprising:

a line store having a capacity for storing a sequence of digital electric signals representing a video line, said line store comprising a set of line store sections each storing a segment of said sequence of digital electric signals, an image store having respective image store sections each with a respective individual input data channel leading to the individual image store section, and having signal output means for the supply of image signals at a video display rate, and a register multiplexer having respective inputs connected with the respective line store sections of said line store, and having respective outputs connected with respective individual input data channels of respective individual image store sections, said register multiplexer in a multiplex cycle loading respective segments representing a video line stored by the set of line store sections in parallel into respective image store sections, and in a series of multiplex cycles loading segments into the image store representing a video image.

2. Apparatus for the storage of successive digital electric signals representing successive video lines, in particular corresponding to ultrasonic images, said apparatus comprising:

a line store having a capacity for storing a sequence of digital electric signals representing a video line, said line store comprising a set of line store sections each storing a segment of said sequence of digital electric signals, an image store having plural series of image store sections with a respective individual input data channel leading to each individual image store section of each series, and each series having a respective common output data channel for supplying stored digital electric signals from any selected one of the image store sections of the respective series, a register multiplexer having respective inputs connected with the respective line store sections of said line store, and having plural outputs for each input connected with respective individual input data channels of individual image store sections of the respective series, said register multiplexer in a first multiplex cycle loading respective segments representing a first video line stored by the set of line store sections in parallel into first respective image store sections of alternately different ones of said series, and in a further multiplex cycle loading respective segments representing a second video line stored by the set of line store sections in parallel into respective different second image store sections of the respective series alternating with the first image store sections in the plural series of image store sections, and said register multiplexer repeating such multiplex cycles to effect storage of plural images in said image store, and control means controlling readout of the image store sections such that in a first readout cycle image store sections of one series then of another series are alternately addressed in sequence to readout the successive segments representing the first video line and in a further readout cycle the respective series are alternately addressed in a reverse order to readout the successive segments representing the second video line and continuing such readout cycles to readout respective stored images from the image store.

3. Apparatus for the storage of successive digital electric signals representing successive signal lines, in particular corresponding to ultrasonic signals, said apparatus comprising:

a line store having a capacity for storing a sequence of digital electric signals representing a signal line, said line store having a serial input and comprising a set of line store sections for storing respective segments of a sequence of digital electric signals representing successive portions of a signal line, a signal store having respective signal store sections each with a respective individual input data channel leading to the individual signal store section, and having signal output means for the supply of stored signals from the signal store sections in a selected sequence at a readout rate consistent with video display of the stored signals, and a register multiplexer having respective inputs connected with the respective line store sections of said line store, and having respective multiplexer outputs connected with respective individual input data channels of respective individual signal store sections, said register multiplexer in a multiplex cycle loading respective segments of a signal line stored by the set of line store sections in parallel into respective signal store sections, and in a series of multiplex cycles loading successive signal lines into said signal store sections for subsequent serial readout of the stored signal lines at said readout rate in constructing a video rate image signal.

4. Apparatus according to claim 3, with said signal store being partitioned into memory subdivisions each having a respective series of said signal store sections, said signal output means comprising a separate signal output for each respective series of signal store sections for selectively receiving stored segments of signal lines from the signal store sections of such respective series, said register multiplexer loading successive segments of each signal line into the signal store sections of alternate ones of the respective series, said output means during a readout cycle supplying segments of a stored signal line alternately from the signal store sections of the respective series so as to supply the stored signal lines at said readout rate in constructing a video rate image signal.

5. Apparatus according to claim 4 with said signal output means of said signal store further comprising a data multiplexer having respective data inputs connected with the respective separate signal outputs of the respective series of signal store sections, said data multiplexer during readout operation alternately activating said data inputs to assemble segments of each stored signal line from the signal store sections of the respective series during the constructing of a video rate image signal therefrom.

6. Apparatus according to claim 3, with said signal store comprising an ultrasonic image memory, said register multiplexer being operable for storing ultrasonic signal lines representing a plurality of ultrasonic images in said signal store.

7. Apparatus according to claim 6, with said output means during readout operation supplying successive segments of a signal line of one ultrasonic image and then of another ultrasonic image alternately in constructing video rate image signals in accordance with the plurality of ultrasonic images stored in said signal store.

8. Apparatus according to claim 4, with said signal store being an ultrasonic image memory having a number of memory subdivisions equal to the number of ultrasonic images to be stored by said signal store, the segments of signal lines of each stored ultrasonic image being distributed to successive signal store sections of the respective series in a predetermined order.

9. Apparatus according to claim 8, with said output means during readout operation supplying successive segments of a signal line of one ultrasonic image and then of another ultrasonic image alternately in constructing video rate image signals in accordance with the plurality of ultrasonic images stored in said signal store.

10. Apparatus according to claim 5 with said signal store comprising an ultrasonic image memory, said signal store sections having a capacity to store a plurality of ultrasonic images, said data multiplexer having a plurality of data outputs which are each alternately connected to the respective data inputs during said readout operation to supply successive lines of one ultrasonic image at one data output and to supply successive lines of another ultrasonic image at another data output.

11. Apparatus according to claim 10 with respective buffer store means connected with the respective data outputs of said data multiplexer such that a line of the one ultrasonic image is loaded into one buffer store means while a line of another ultrasonic image previously loaded into another of the respective buffer store means is being read out at a video line rate, such that both ultrasonic images can be simultaneously displayed.

12. Apparatus according to claim 3, with said signal store having two series of signal store sections, one series having first and third image store sections for storing first and third segments of first image lines of a first image, and having second and fourth signal store sections for storing second and fourth segments of second image lines of a second image, the other series having first and third signal store sections for storing first and third segments of the second image lines of the second image, and having second and fourth signal store sections for storing second and fourth segments of the first image lines of the first image.

13. Apparatus according to claim 3, with the respective segments of each signal line being written into the signal store in programmable formation.

14. Apparatus according to claim 13, with the writing into the signal store being programmed so that it is possible temporarily to switch over as required from the parallel transfer of segments of signal lines into the signal store to series transfer.

15. Apparatus according to claim 13, with said signal output means being programmable so that specific signal store sections allotted to different image scanning modes are capable of being read out.

16. Apparatus according to claim 15, with the signal store sections of the signal store being capable of storing different signals representing different image scanning modes, which signals may be read out singly or in combination.

17. An arrangement according to claim 3, with the signal store being an ultrasonic image store which may be programmed so that a single ultrasonic image or several ultrasonic images may be read in.

18. Apparatus according to claim 17 with said signal output means being such that with several ultrasonic output means the read out takes place according to program so that the images may be represented, in any configuration relative to one another, simultaneously on an image display.

19. Apparatus according to claim 18, with said signal output means being such that at least two images may be represented next to each other or over each other.

20. Apparatus according to claim 18, with said signal output means being such that when at least two images are represented one is a stored image and the other a real-time image.

21. Apparatus according to claim 17, with said output means being such that at least one B-image may be represented simultaneously with one TM-image.

* * * * *